United States Patent
Oloman et al.

(10) Patent No.: US 6,299,743 B1
(45) Date of Patent: Oct. 9, 2001

(54) ELECTROLYTIC GENERATION OF NITROGEN

(75) Inventors: Colin Oloman, Vancouver; Jiujun Zhang; Jielin Song, both of Delta, all of (CA)

(73) Assignee: A.T.S. Electro-Lube Holdings, Ltd/, British Columbia (CA)

(*) Notice: Subject to any disclaimer, the term of this patent is extended or adjusted under 35 U.S.C. 154(b) by 0 days.

(21) Appl. No.: 09/353,245

(22) Filed: Jul. 14, 1999

(30) Foreign Application Priority Data

Jul. 14, 1998 (CA) .................................................. 2243219

(51) Int. Cl.[7] ................. C25B 9/00; C25C 7/00; C25D 17/00

(52) U.S. Cl. .................... 204/252; 205/780.5; 205/617

(58) Field of Search .................. 205/551, 617, 205/780.5; 204/252, 295, 291, 283

(56) References Cited

U.S. PATENT DOCUMENTS

| | | |
|---|---|---|
| 1,561,308 | 11/1925 | Brown . |
| 1,878,115 | 9/1932 | De Cosse . |
| 3,256,504 | 6/1966 | Fidelman . |
| 3,374,158 | 3/1968 | Lord et al. . |
| 3,424,022 | 1/1969 | Greenberg et al. . |
| 3,739,573 | 6/1973 | Giner . |
| 3,822,607 | 7/1974 | Tharaldsen . |
| 3,840,454 | 10/1974 | Jansta et al. . |
| 3,870,616 | 3/1975 | Dempsey et al. . |
| 4,023,648 | 5/1977 | Orlitzky et al. . |
| 4,057,479 | 11/1977 | Campbell . |
| 4,146,446 | 3/1979 | von Sturm . |
| 4,288,913 | 9/1981 | Parsen et al. . |
| 4,328,843 | 5/1982 | Fujii . |
| 4,337,140 | 6/1982 | Solomon . |
| 4,388,163 * | 6/1983 | Richter et al. ................... 205/555 |
| 4,414,071 | 11/1983 | Cameron et al. . |
| 4,424,105 | 1/1984 | Hanson . |
| 4,455,358 | 6/1984 | Graham et al. . |
| 4,534,837 | 8/1985 | Nicolas et al. . |
| 4,671,386 | 6/1987 | Orlitzky . |
| 4,737,257 | 4/1988 | Boulton . |
| 4,784,730 | 11/1988 | Willis et al. . |
| 5,089,107 | 2/1992 | Pacheco . |
| 5,242,033 | 9/1993 | Toraason . |
| 5,242,565 | 9/1993 | Winsel . |
| 5,285,871 | 2/1994 | Sievenpiper . |
| 5,354,264 | 10/1994 | Bae et al. . |
| 5,395,709 | 3/1995 | Bowker et al. . |

(List continued on next page.)

FOREIGN PATENT DOCUMENTS

| | | |
|---|---|---|
| 1266622 | 3/1990 | (CA) . |
| 133579 | 12/1994 | (CA) . |
| 567679 | 10/1975 | (CH) . |
| 561250 | 5/1944 | (GB) . |
| 1710890 A1 | 2/1992 | (SU) . |

OTHER PUBLICATIONS

Supin et al. (Polarographic Behavior of Organic Hydrazines. Oxydiation of Acetyl–and Arylhydrazides on a Mercury Electrode, Zh. Obshch. Khim. (Mar. 1978), 48(3), 698–9).*

*Primary Examiner*—Kathryn Gorgos
*Assistant Examiner*—Wesley A. Nicolas
(74) *Attorney, Agent, or Firm*—James W. McClain; Brown, Martin, Haller & McClain, LLP

(57) ABSTRACT

The invention provides methods and devices for the electrochemical generation of nitrogen from organic nitrogen compounds, such as hydrazides ($RCONHNH_2$), the corresponding organic hydrazino-carboxylates ($RCO_2NHNH_2$) and amino-guanidine salts (e.g. aminoguanide bicarbonate $H_2NNHC(NH)NH_2 \cdot H_2CO_3$). In the hydrazides and hydrazino-carboxylates, "R" may be an alkyl, alkenyl, alkynyl or aryl group, in some embodiments methyl, ethyl, or benzyl. The alkyl, alkenyl and alkynyl groups may be branched or unbranched, substituted or unsubstituted.

38 Claims, 6 Drawing Sheets

U.S. PATENT DOCUMENTS

| | | |
|---|---|---|
| 5,401,371 | 3/1995 | Oshima et al. . |
| 5,404,966 | 4/1995 | Yang . |
| 5,409,084 | 4/1995 | Graf . |
| 5,417,308 | 5/1995 | Hartl . |
| 5,423,454 | 6/1995 | Lippman et al. . |
| 5,427,870 | 6/1995 | Joshi et al. . |
| 5,460,242 | 10/1995 | Graf . |
| 5,527,642 | 6/1996 | Meadows et al. . |
| 5,538,605 | 7/1996 | Joshi et al. . |
| 5,547,043 | 8/1996 | Graf et al. . |
| 5,567,284 | 10/1996 | Bauer et al. . |
| 5,567,287 | 10/1996 | Joshi et al. . |
| 5,573,646 | 11/1996 | Saito et al. . |
| 5,585,208 | 12/1996 | Lian et al. . |
| 5,593,552 | 1/1997 | Joshi et al. . |

\* cited by examiner

ELECTROLYTIC GENERATION OF NITROGEN

FIELD OF THE INVENTION

The invention is in the field of methods and apparatus for electrochemical generation of nitrogen and hydrogen gases. Particularly generation of nitrogen gas from organic hydrazides ($RCONHNH_2$) and hydrazino-carboxylates ($RCOONHNH_2$), and amino guanidine salts, circuits for spontaneous oxidation of such nitrogen compounds to generate nitrogen gas and mechanical transducers actuated by the nitrogen gas so produced, particularly in the field of fluid dispensers.

BACKGROUND OF THE INVENTION

The controlled electrolytic generation of gases is useful to convert chemical to mechanical energy in a variety of applications. For example, a variety of lubricant or fluid delivery systems driven by the electrolytic generation of a gas are known. For example, U.S. Pat. No. 4,023,648 to Orlitzky et al. (1977) shows a lubricant applicator driven by gas generated in an electrochemical cell and provides a method for the electrochemical generation of hydrogen gas.

Fluid dispensers driven by electrochemically generated gases, and other electrochemical transducers may often be used in circumstances which give rise to special operational requirements. Typically, components of any electrolytic cell used in such an application must be stable over time and over a range of temperatures. In such devices, it is undesirable to have highly reactive gases generated, such as hydrogen or oxygen. Once the circuits are closed to initiate electrolytic gas generation, it is desirable to have relatively fast electrode reactions with low overpotential (i.e. a small difference between the electrode potential under electrolysis conditions and the thermodynamic value of the electrode potential in the absence of electrolysis), small concentration polarisation of solutes across the cell (i.e. rapid diffusion of reactants to the electrode surfaces), and small separator resistance effects (i.e. little resistance caused by solid separators within the cell. It is also desirable to produce gases from a small amount of material, i.e. to have efficient gas generation and high stoichiometric coefficients for gaseous reaction products.

Hydrogen and oxygen gases are used in a variety of known electrochemical gas generators. One disadvantage of such systems is the chemical reactivity of those gases. Another disadvantage of hydrogen in particular is that it diffuses relatively rapidly through a variety of polymeric barriers that might otherwise be used to contain the electrolytically generated gas in a mechanical transducer, such as a fluid dispenser.

Nitrogen is a relatively inert gas that may usefully be produced by electrolytic reactions to provide controlled amounts of gas. However, existing methods for the electrolytic generation of nitrogen suffer from a number of disadvantages.

U.S. Pat. No. 5,567,287 issued to Joshi et al. (1996) discloses a solid state electrochemical nitrogen gas generator for fluid dispensing applications. Nitrogen is produced in that system by the electro-oxidation of a decomposable solid material of the generic formula $A_xN_y$ in a divided electrochemical cell, where "A" is an alkali metal such as sodium or lithium, "N" is nitrogen, x is 1 to 3 and y is 1 to 3. Example compounds disclosed therein include $LiN_3$ (lithium nitride) and $NaN_3$ (sodium azide). The azide half cell reaction in such a system (reaction 1) may however be slow, in part because of the high overpotential required for the electro-oxidation of azide.

$$2N^{3-} \rightarrow 3N_2 + 2e^- \quad (1)$$

To overcome the problem of the sluggish kinetics of the azide half-cell, additives such as thiocyanate may be used to catalyse the iodine mediated formation of nitrogen from azides, as in reactions 2 and 3:

$$2I^- \rightarrow I_2 + 2e^- \quad (2)$$

$$I_2 + 2N_3^- \xrightarrow{SCN^-} 2I^- + 3N_2 \quad (3)$$

However, such systems suffer from the disadvantages that azides are toxic and the thiocyanate salt catalysts are also toxic. The presence of toxic compounds may make it difficult to dispose of a device which generates nitrogen gas from azides.

SUMMARY OF THE INVENTION

The invention provides methods and devices for the electrochemical generation of nitrogen from organic nitrogen compounds, such as hydrazides ($RCONHNH_2$), the corresponding organic hydrazino-carboxylates ($RCO_2NHNH_2$) and amino-guanidine salts (e.g. aminoguanide bicarbonate $H_2NNHC(NH)NH_2 \cdot H_2CO_3$). A variety of organic hydrazides and hydrazino-carboxylates may be used, and empirically tested for performance. For example, in the hydrazides and hydrazino-carboxylates "R" may be selected from suitable alkyl, alkenyl, alkynyl or aryl groups, in some embodiments methyl, ethyl, or benzyl. The alkyl, alkenyl and alkynyl groups may be branched or unbranched, substituted or unsubstituted. Some such compounds may not work in all embodiments, as determined by routine functional testing. The utility of such compounds may, for example, be routinely assayed in accordance with the guidance provided herein, including the Examples set out herein in which alternative nitrogen compounds may be substituted for routine test purposes.

The present invention also provides methods and devices for the auto-electrolytic generation of nitrogen, using electrochemical cells that comprise both a nitrogen compound capable of acting as a reductant in an electrochemical reaction to produce nitrogen gas, and an electrochemical oxidant capable of driving the oxidation of the nitrogen compound.

The present invention also provides a housing for electrochemical gas generating cells. The housing acts to compress a flexible electrochemical cell to help maintain electrochemical contacts in the cell over a prolonged period of operation, during which the compositions within the cell may contract while gas is evolved from the cell. The housings of the invention may be used with a wide variety of gas-generating electrochemical cells, including hydrogen, oxygen and nitrogen generating cells.

The housings of the invention may also be adapted to enclose a plurality of cells, in which case the cells may be arranged in series to increase the potential drop across the cells. There may be advantages associated with arranging electrochemical gas generating cells in series to increase the potential of the circuit, particularly when the cells are to be used in fluid dispensers. A higher potential difference across the cells allows for the use of a larger (and in some embodiments variable) resistance in the circuit of the electrochemical cell. The larger the resistance, the less sensitive the circuit is to variations in temperature.

The sensitivity of the circuit (the electrochemical cell and the external electronic components) to temperature change generally comes about as a result of the fact that increasing temperature will generally decrease the effective resistance of the electrochemical cell and increase the current in the circuit. However, increasing temperature will normally increase the resistance of the electronic components of the circuit (i.e. the external electronic resistance) and this partially compensates for the effect of temperature on the electrochemical cell. In other words, the temperature coefficient of resistivity of the electrochemical cell, which is an ionic resistance, is negative, whereas the temperature coefficient of resistivity of the external circuit, which is an electronic resistance, is usually positive (although of a lower order of magnitude than for the cell). Providing for operation with a greater potential in the circuit allows the circuit to include a higher external electronic resistance, and thus makes the circuit less sensitive to temperature changes. In a fluid dispenser, it is generally desirable to provide a constant current that does not fluctuate substantially with temperature in order to provide a constant flow of fluid. Of course, if it is desired to make the circuit temperature sensitive, this may also be accomplished in accordance with the circuits of the invention.

DETAILED DESCRIPTION OF THE INVENTION

Figure 4A:
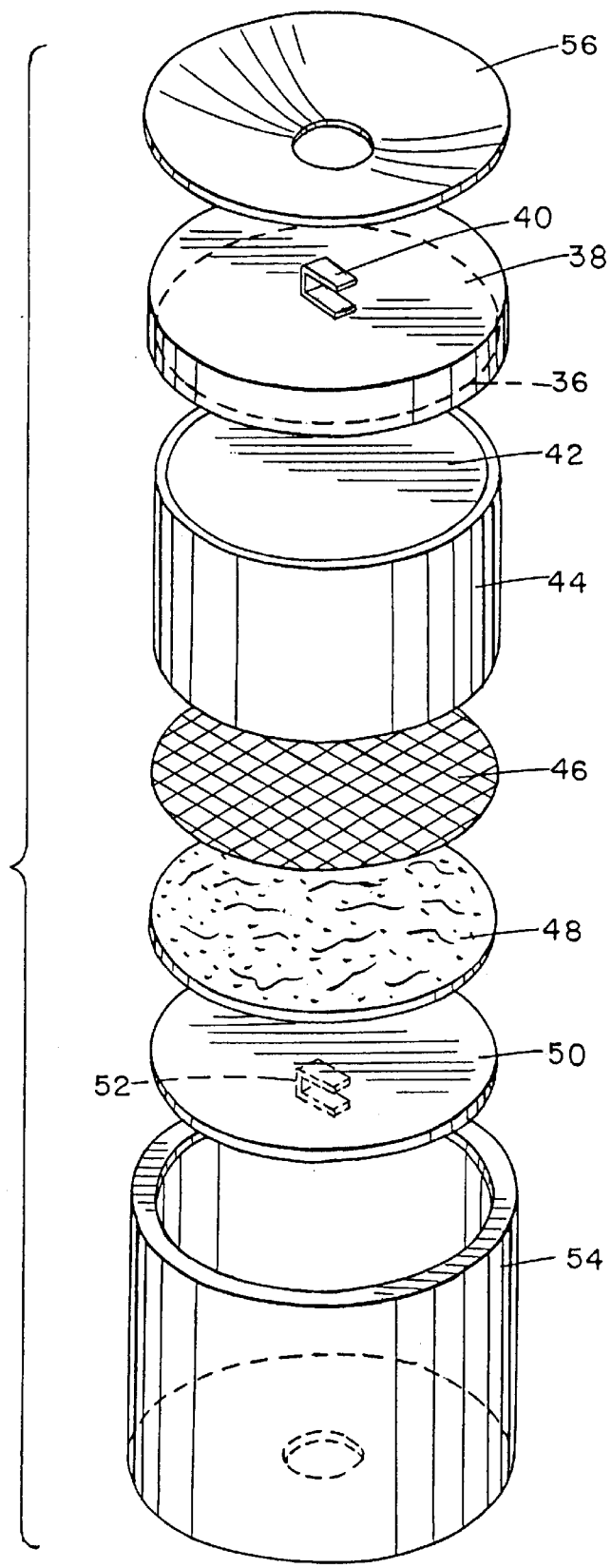
FIG. 4A is an exploded isometric view of a housing for an electrolytic cell.
Figure 4B:
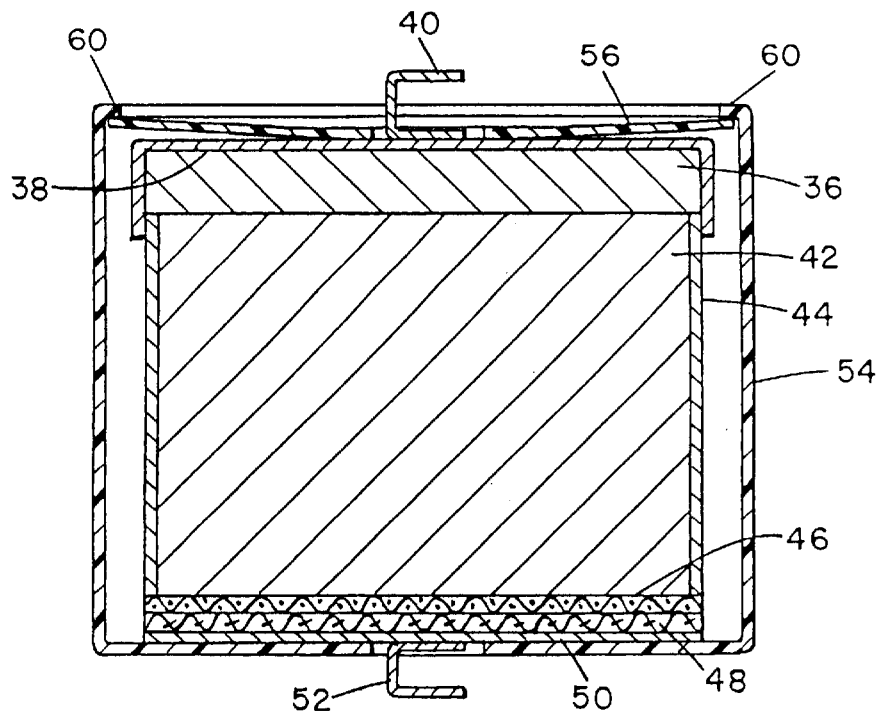
FIG. 4B is a side elevational view of a housing for an electrolytic cell.
Figure 5:
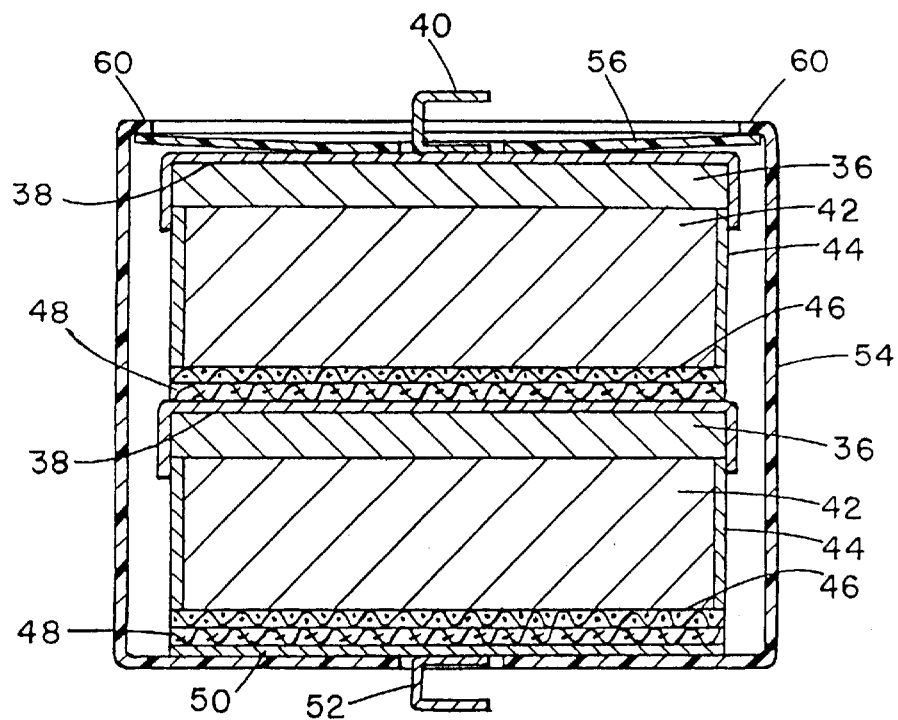
FIG. 5 is a side elevational view of a housing for an electrolytic cell.

The generation of nitrogen using the methods of the present invention may be particularly useful in electrochemically driven fluid dispensers. For example, FIG. 1 illustrate a dispenser for a fluid 10. The dispenser has a body 12 and an outlet nozzle 14. There is a piston 16 and a bellows 18 to force the fluid 10 from the nozzle 14. The necessary force is generated by an electrolytic gas generator 20 having an external circuit that includes a resistor 22, battery 26 and a switch 24. FIGS. 4A and 4B illustrate alternative embodiments of electrochemical cells according to various aspects of the invention. Such cells may be made of a sandwich construction comprising an anode 36, such as a gelled anode, in a conductive cup 38, such as a brass cup, having a contact 40 to enable wiring t an external circuit. An electrolyte 42 is contained in a thin-walled tube 44. A permeable cathode, such as a screen 46 backed by a graphite felt 48 and a brass disk current collector 50 may be used, with a contact 52 to enable wiring to the external circuit. The cell may be contained in a polypropylene cylinder 54. A spring washer 56 on cup 38 may be retained by a lip 60 on cylinder 54. FIG. 5 shows the configuration of a bipolar cell, in which cells such as those illustrated in FIGS. 4A and 4B are compressed in series with electronic contact between adjacent anodes and cathodes, for example by spring loading of washer 56. Brass plate current collectors 50 and contacts 52 are omitted from all cathodes except the end cathode.

In the cells shown in FIGS. 4A, 4B and 5, thin-walled tube 44 may be selected to be sufficiently flexible to permit compression of the cells, such as by spring washer 56, as reactants in electrolyte 42 and anode 36 are depleted. Such compression may help to ensure that good electrical contact is maintained, for example between electrolyte 42 and anode 36. A sealed connection between tube 44 and cap 38 may be preferred to avoid loss of electrolyte and short-circuiting of the bipolar cells. In one aspect, the invention accordingly provides a housing for an electrolytic cell comprising an anode, a cathode and an electrolyte biased together in electrical contact, the electrolyte being contained by a flexible membrane adapted to accommodate compression of the electrolyte, the housing having an opening to permit passage of gas evolved from the electrolyte during electrolysis.

A permeable cathode, for example comprised as illustrated of a screen 46 backed by a graphite felt 48, is useful to permit egress of gas into the space defined by container 54. Electrolyte 42 may preferably be adapted to be sufficiently viscous or solid to operate in combination with a permeable cathode to allow gas to be evolved from the cathode, but to prevent loss of electrolyte. The electrolyte should however be sufficiently liquid to permit adequate mass transfer to provide for a desired rate of gas evolution. A variety of absorbent materials or gelling agents may be used to stabilise the electrolyte against leakage, including hydrophilic absorbent materials such as cellulose sponges, cotton wool, synthetic felts, diato-maceous earth; and gelling agents such as carbopol, carboxymethylcellulose and others.

The electrolyte solution should contain an ionic compound (salt, acid or base) capable of mediating electrical conductivity. An electrolyte compound may also provide antifreeze properties. In some embodiments, antifreeze properties may be associated with the use of inorganic electrolytes such as sodium chloride, calcium chloride, sulphuric acid or ammonium sulphate. An organic antifreeze agent may also be added to the electrolyte to depress its freezing point. In some embodiments, examples of organic antifreezes may include ethylene glycol, dimethyl sulphoxide, methanol, ethanol or urea.

As set out particularly in Examples 6 through 9 herein, additives may be used in the electrolyte in undivided cells to facilitate the generation of nitrogen at the anode while suppressing the co-generation of hydrogen on the cathode. A typical cathode reaction in an undivided cell (such as those shown in FIGS. 1B, 4A and 4B) is the generation of hydrogen by electro-reduction of water:

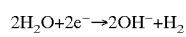

Hydrogen is however an undesirable product in some devices, such as certain lubricant dispensers, for the reasons discussed in the background section herein. It may accordingly be useful to use additives in an electrolyte that will react preferentially at the cathode to suppress the evolution of hydrogen, such compounds are termed herein "cathode depolarisers." Examples 6 through 9 disclose particular embodiments of such compounds. In some embodiments, preferred cathode depolarisers will not be reduced to products that suppress the evolution of nitrogen at the anode.

In various embodiments, the invention provides a variety of alternative cathode depolarisers, such as cupric salts, nitroguanidine, nitroethanol and nitromethane. The performance of candidate cathode depolarisers may be determined empirically in the context of a particular electrolytic cell. Preferred depolarisers may be obtained where the electroreduction at the cathode is substantially irreversible. Some depolarisers may not work well under some conditions, such as low temperature (for example below −25° C.). Some cathode depolarisers, such as some copper salts, may promote the spontaneous decomposition of some organic nitrogen compounds, such as methyl hydrazino-carboxylate, to nitrogen (a reaction that may compromise the shelf life of cells containing these reactants). Potential cathode reactions of exemplified depolarisers are set out below (although this information may assist others in identifying other members of this class of compounds, they do not necessarily represent the true or complete nature of the cathode reactions - which are not all known):

1. Cupric Salts, i.e. $Cu^{++}$ (e.g. cupric sulphate, as set out in Examples 4 and 5):

$$Cu^{++} + 2e^- \rightarrow Cu$$

2. Nitroguanidine, i.e. $NH_2(NH)CHNNO_2$ $$NH_2(NH)CHNNO_2 + 6H^+ + 6e^- \rightarrow NH_2(NH)CHNNH_2 + 2H_2O$$

3. Nitroethanol, i.e. $OHCH_2CH_2NO_2$ $$OHCH_2CH_2NO_2 + 6H + 6e^- \rightarrow OHCH_2CH_2NH_2 + 2H_2O$$

4. Nitromethane, i.e. $CH_3NO_2$ $$CH_3NO_2 + 6H^+ + 6e^- \rightarrow CH_3NH_2 + 2H_2O$$

EXAMPLE 1

Figure 1A:
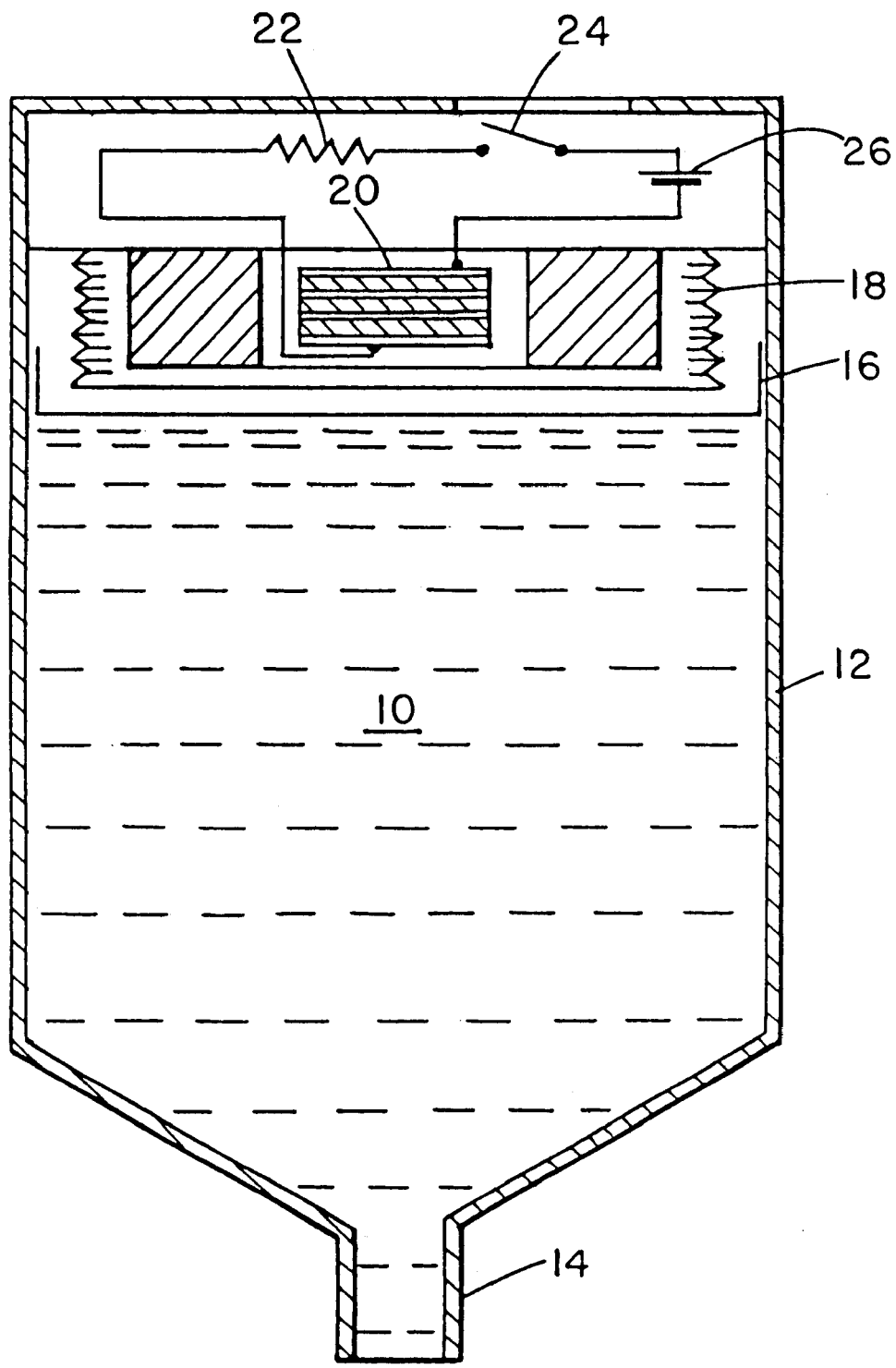
FIG. 1A is a schematic side elevational view of a fluid dispenser.
Figure 1B:
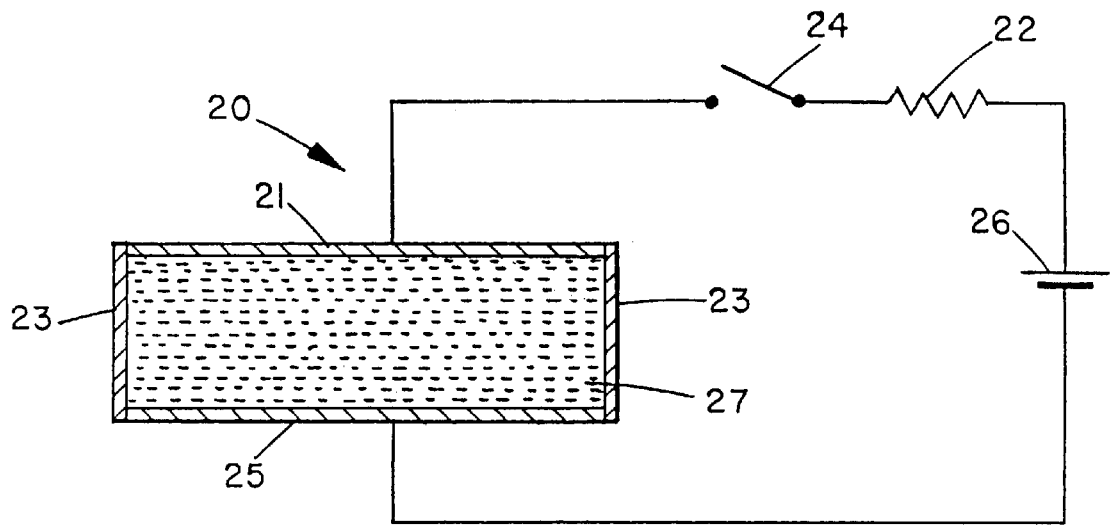
FIG 1B is a schematic cross-sectional view of an electrical circuit including an electrolytic cell.

In one embodiment, a nitrogen gas generator is assembled as shown in FIG. 1B, comprising:
(a) a circuit comprising an external energy source 26, such as two 1.5 V alkaline batteries connected in series; a resistor 22, such as a variable resistor from 1 to 100 kohm; and a switch 24;
(b) an undivided electrochemical cell 20 comprising:
  i) electrolyte solution 27, comprising an active nitrogen compound, in one embodiment, methyl hydrazine carboxylate (about 0.1 to 4M), urea (about 0.1 to 1M), ammonium sulphate (about 0.1 to 2M) and water, all absorbed in a cellulose sponge;
  ii) anode 21 and cathode 25, which in various embodiments may be graphite fibre impregnated with a polymer such as Nylon™ or polypropylene, GRAFOIL, pyrolytic carbon, carbon black, platinum or gold.

The probable (but unknown) methyl hydrazino-carboxylate anode reaction (as in examples 6, 8 and 9) is:

$$CH_3CO_2NHNH_2 \rightarrow CH_3CO_2H + N_2 + 2H^+ + 2e^-$$

In such an embodiment, when switch 24 is closed to turn the circuit on, with a resistance 12 of 6 kOhm, this cell generated about 2.5 ml STP of gas per day over a period of 14 days at 23° C.

EXAMPLE 2

Figure 2:
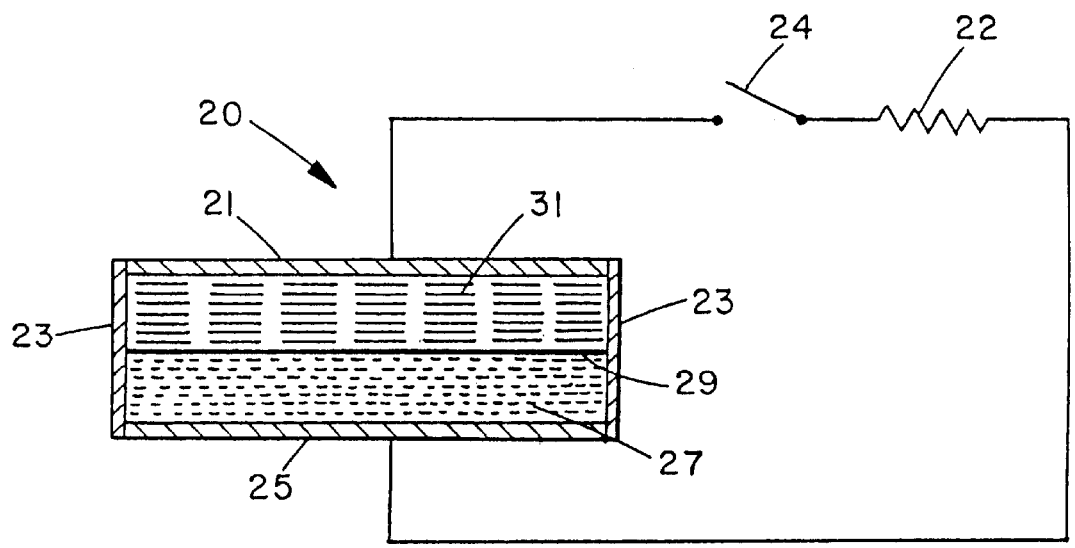
FIG. 2 is a schematic cross-sectional view of an electrical circuit including an electrolytic cell.

In another embodiment, a nitrogen generator was assembled according to FIG. 2 and consisted of:

(a) an external electronic circuit comprising switch 24 with a resistor 22, which may be a variable resistor;
(b) an electrochemical cell 29 divided by a cation membrane 29 (such as the sulfonated perfluoroethylene polymer sold under the trade-mark NAFION 324 by E.I. DuPont & DeNemours Co., Wilmington, Del., U.S.A., or equivalents thereof) with:
  i) a catholyte 27 of a solution of sodium bromate in aqueous sulphuric acid;
  ii) an anolyte mixture of sodium azide (about 0.1 to 4M), sodium bicarbonate (about 0.1 to 1M), sodium iodide (about 0.1 to 1M) and sodium thiocyanate (about 0.1 to 1M) in water;
  iii) electrodes of Nylon™ impregnated graphite fibre and GRAFOIL (such as the product sold under the trade-mark GRAFOIL GTB by Union Carbide Corp.).

The putative reaction at the cathode is:

$$BrO_3^- + 6H^+ + 6e^- \rightarrow Br^- + 3H_2O$$

This cell showed an open circuit (zero current) voltage of 0.73 volt under ambient conditions (i.e. about 22° C., 101 kPa) and when the circuit was closed through a 2 kOhm resistor the current and voltage varied respectively from approximately 0.3 to 0.1 mA and 0.6 to 0.2 volt over a period of 40 days. The azide oxidation reaction is catalysed by the iodide/thiocyanate system. The putative net anode reaction for the azide is:

$$2N_3^- \rightarrow 3N_2 + 2e^-$$

EXAMPLE 3

In an alternative embodiment, a nitrogen generator was assembled according to FIG. 2 and consisted of:
(a) an external electronic circuit comprising switch 24 with a resistor 22, which may be a variable resistor;
(b) a cathode 25 of graphite in contact with an oxidant 27 consisting of a paste of manganese dioxide in aqueous sulphuric acid (about 1 to 4M);
(c) an anolyte mixture 31 of oxalic dihydrazide (about 0.1 to 1M) in aqueous sulphuric acid (about 0.1 to 1M);
(d) an anode 21 of graphite.

On open circuit, this cell showed a voltage of 0.8 volt and no gas was generated at either electrode over a period of several days. When the circuit was closed, gas (nitrogen) was generated at the anode. The probable (but unknown) electrode reactions are:

Anode: $H_2NNHCOCONHNH_2 \rightarrow CO_2 + 2N_2 + 4H^+ + 4e^-$

Cathode: $MnO_2 + 4H^+ + 2e^- \rightarrow Mn^{++} + 2H_2O$

EXAMPLE 4

Figure 3:
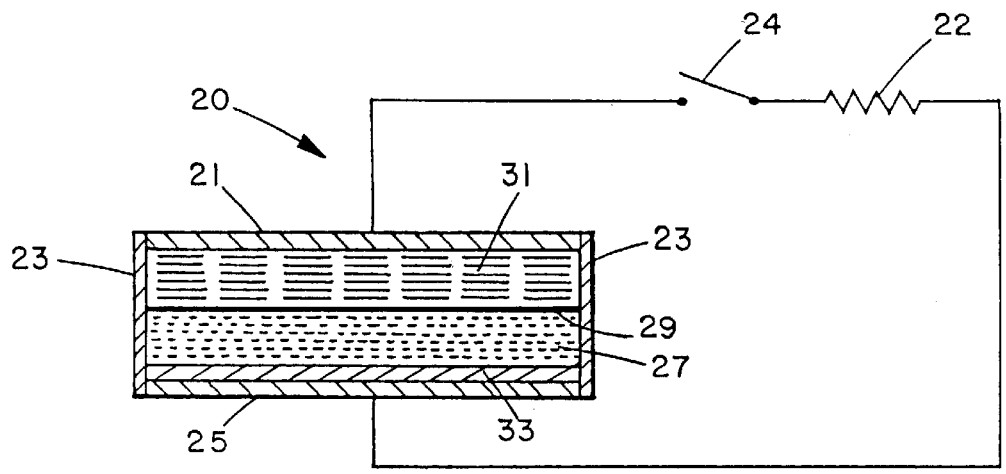
FIG. 3 is a schematic cross-sectional view of an electrical circuit including an electrolytic cell.

In an alternative embodiment, a nitrogen generator was assembled according to FIG. 3 and consisted of:
(a) an external electronic circuit with variable resistance, as in Examples 2 and 3;
(b) a bipolar electrochemical unit with 2 cells:
  i) a first cathode 25 of Nylon™ impregnated graphite fibre with an oxidant 33 paste of manganese dioxide plus carbon powder;
  ii) a catholyte 27 of sulphuric acid (about 1 to 4M) in water absorbed in a cellulose felt;
  iii) a bipole electrode 29 of copper sheet;
  iv) an anolyte 31 mixture of:

cupric sulphate (about 0.1 to 1M);
sulphuric acid (about 0.1 to 1M)
methyl hydrazino-carboxylate (about 0.1 to 2M);
water;
v) an anode 21 of graphite.

For which the anode reaction is uncertain and the putative cathode reaction is:

$$MnO_2+4H^++2e^-\rightarrow Mn^{+2}+2H_2O$$

A bipolar electrode is one without electronic connection to the current supply, one face of which acts as an anode surface and the opposite face of which acts as a cathode surface when an electric current is passed through the cell.

On open circuit (zero current), this unit produced a voltage of 0.54 volt. The circuit was closed through a resistor of 1 kOhm and over a period of 90 days the current ranged from 0.5 to 0.25 mA while the voltage dropped from about 0.5 to 0.25 volt and gas was generated spontaneously at a rate of about 0.15 millimole/day (i.e. 3.4 ml STP/day). This rate of gas generation corresponds to about 100% currency efficiency for a putative methyl hydrazino-carboxylate anode reaction 5.

$$CH_3CO_2NHNH_2 \rightarrow CH_3CO_2H+N_2+2H^++2e^- \tag{5}$$

The cathodic generation of hydrogen is suppressed by a depolariser for depolarising the bipolar electrode, such as a copper salt like cupric sulfate, which may mediate the preferential electrodeposition of copper on the copper bipole by reaction 6.

$$Cu^{++}+2e^-\rightarrow Cu \tag{6}$$

EXAMPLE 5

Figure 4:
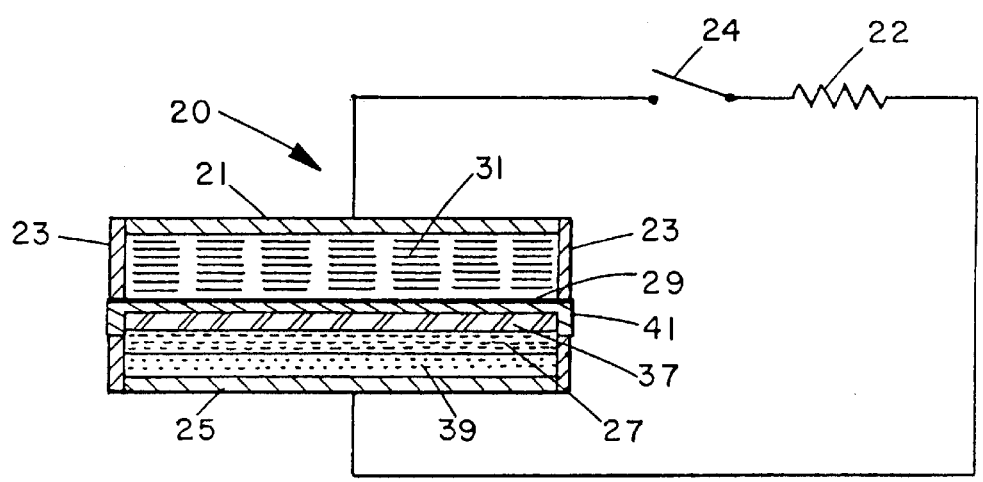
FIG. 4 is a schematic cross-sectional view of an electrical circuit including an electrolytic cell.

In a further alternative embodiment, a nitrogen generator was assembled according to FIG. 4 and consisted of:
(a) an external electronic circuit with variable resistance, as in examples 2 through 4;
(b) a bipole electrochemical unit with 2 cells:
  i) a first anode 21 of "Grafoil" graphite sheet;
  ii) a first electrolyte 31 consisting of a gelled mixture of:
    methyl hydrazino carboxylate (about 0.1 to 4M);
    cupric sulphate (about 0.1 to 1M);
    acetic acid (about 0.1 to 1M);
    water;
  iii) a bipole conductor 29 of Grafoil sheet;
  iv) a second anode 37 of gelled zinc particles in a brass cup 41;
  v) a second electrolyte 27 of gel (such as 30% by weight CARBOPOL gelling agent, potassium hydroxide solution (plus additives));
  vi) an oxidant 39 such as a paste of manganese dioxide with carbon powder (in about 30% by weight KOH);

On open circuit at 23° C., this unit gave a voltage of about 1.2 volt and produced 10 ml STP of gas in 7 days. When the circuit was closed though a 1 kOhm resistor a current of 0.01 mA gave 8 ml STP of gas in two days. The putative electrode reactions in this bipolar unit are:

First anode: $CH_3CO_2NHNH_2 \rightarrow CH_3CO_2H+N_2+2H^++2e^-$

First cathode: $Cu^{++}+2e^-\rightarrow Cu$

Second anode: $Zn\rightarrow Zn^{++}+2e^-$

Second cathode: $MnO_2+4H^++2e^-\rightarrow Mn^{++}+2H_2O$

EXAMPLE 6

A nitrogen gas generator was assembled as in FIG. 1B, comprising:

a. A circuit with two alkaline 1.5 V batteries connected in series (26), a 3 kOhm resistor (22) and a switch (24);
b. An undivided electrochemical cell (20) with:
  i. about 15 ml of an electrolyte solution (27) absorbed in a cellulose sponge, composed of approximately:
    2.7 grams methyl hydrazino-carboxylate (anode reactant);
    3.5 g sodium chloride (electrolyte);
    3.9 g nitroguanidine (cathode depolariser); and,
    water;
  ii. an anode (21) and cathode (25), each composed of Nylon™ impregnated graphite fibre.

This nitrogen generating cell was inserted into a commercial automatic lubricant dispenser (ATS Electro-Lube MINI-LUBER) as shown in FIG. 1A (with 2 1.5V batteries used in the external circuit). The dispenser was loaded initially with about 100 grams of grease (10), with a density of about 900 kg/m³. Switch (24) was closed to turn the circuit on, and the unit operated at room temperature and zero kPa(gauge) grease outlet pressure. The consequent grease dispensing rate averaged about 4 cc/day over a 14 day period. The approximate composition of total gas produced by the electrochemical cell over 14 days was as shown in Table 1.

TABLE 1

| Gas Production | |
|---|---|
| Component | Volume % (dry basis) |
| hydrogen | 0.0 |
| oxygen | 1.0 |
| nitrogen | 96.0 |
| methane | 2.0 |
| carbon monoxide | 1.0 |

EXAMPLE 7

A nitrogen gas generator was assembled as in FIG. 1B, comprising:

a. A circuit with two alkaline 1.5 V batteries connected in series (26), a 3 kOhm resistor (22) and a switch (24); and,
b. An undivided electrochemical cell (20) comprising:
  i. about 15 ml of an electrolyte solution (27) absorbed in a cellulose sponge, composed of approximately:
    4 grams aminoguanidine bicarbonate (anode reactant);
    3.5 g sodium chloride (electrolyte);
    2.7 g nitroethanol (cathode depolariser); and,
    water;
  ii. an anode (21) and cathode (25), each composed of Nylon™ impregnated graphite fibre.

This nitrogen generating cell was inserted into a commercial automatic lubricant dispenser (ATS Electro-Lube MINI-LUBER) as shown in FIG. 1A (with two, 1.5V batteries 26 used in the external circuit). The dispenser was loaded initially with about 100 grams of grease (10), with a density of about 900 kg/m³. Switch (24) was closed to turn the circuit on, and the unit operated at room temperature and zero kPa (gauge) grease outlet pressure. The consequent grease dispensing rate averaged about 2.8 cc/day over a 14 day period. The approximate composition of total gas produced by the electrochemical cell over 14 days was as shown in Table 2.

TABLE 2

Gas Production

| Component | Volume % (dry basis) |
|---|---|
| hydrogen | 0.0 |
| oxygen | 2.0 |
| nitrogen | 95.0 |
| methane | — |
| carbon monoxide | 2.0 |

The anode reaction is presumably the electro-oxidation of amino-guanidine bicarbonate to nitrogen (with unknown side products).

EXAMPLE 8

A nitrogen gas generator was assembled as in FIG. 1B, comprising:
a. A circuit with two alkaline 1.5 V batteries connected in series (26), a 3 kOhm resistor (22) and a switch (24);
b. An undivided electrochemical cell (20) with:
   i. about 15 ml of an electrolyte solution (27) absorbed in a cellulose sponge, composed of approximately:
      16 wt % methyl hydrazino-carboxylate (anode reactant);
      16 wt % sodium chloride (electrolyte);
      16 wt % nitroethanol (cathode depolariser);
      20 wt % ethylene glycol (antifreeze) and, 32 wt % water;
   ii an anode (21) and cathode (25), each composed of Nylon™ impregnated graphite fibre.

This nitrogen generating cell was inserted into a commercial automatic lubricant dispenser (ATS Electro-Lube MINI-LUBER) as shown in FIG. 1A (with 2 1.5V batteries used in the external circuit). The dispenser was loaded initially with about 100 grams of grease (10), with a density of about 900 kg/m³. Switch (24) was closed to turn the circuit on, and the unit operated at room temperature and zero kPa(gauge) grease outlet pressure. The consequent grease dispensing rate ranged from about 2.8 cc/day to 0.4 cc/day over a 21 day period. The approximate composition of total gas produced by the electrochemical cell over 21 days was as shown in Table 3.

TABLE 3

Gas Production

| Component | Volume % (dry basis) |
|---|---|
| hydrogen | 0.0 |
| oxygen | 0.7 |
| nitrogen | 88.1 |
| methane | 0 |
| carbon monoxide | 0.9 |
| carbon dioxide | 4.6 |
| nitrous oxide | 5.8 |

EXAMPLE 9

A nitrogen gas generator was assembled as in FIG. 1B, comprising:
a. A circuit with two alkaline 1.5 V batteries connected in series (26), a 3 kOhm resistor (22) and a switch (24);
b. An undivided electrochemical cell (20) with:
   i. about 15 ml of an electrolyte solution (27) absorbed in a cellulose sponge, composed of approximately:
      2.7 grams methyl hydrazino-carboxylate (anode reactant);
      2.7 g sodium chloride (electrolyte);
      2.7 g nitromethane (cathode depolariser);
      3.0 g ethylene glycol (antifreeze);
      3.0 g dimethyl sulphoxide (antifreeze); and, water;
   ii. an anode (21) and cathode (25), each composed of Nylon™ impregnated graphite fibre.

Figure 6:
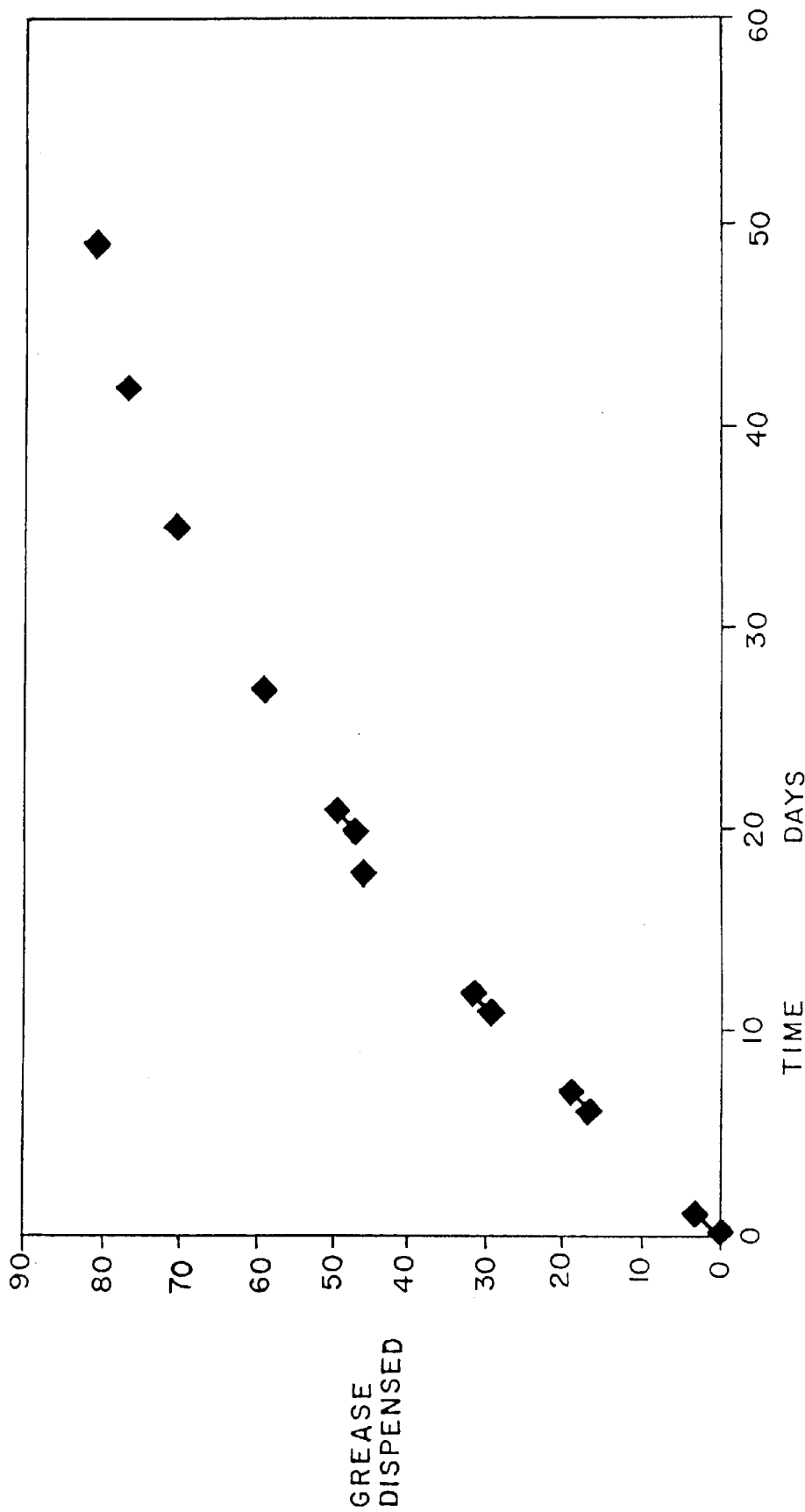
FIG. 6 is a graph showing a plot of the volume of grease dispensed as a function of time for a lubricant dispenser driven by the electrochemical nitrogen generator of Example 9.

This nitrogen generating cell was inserted into a commercial automatic lubricant dispenser (ATS Electro-Lube MINI-LUBER) as shown in FIG. 1A (with 2 1.5V batteries used in the external circuit). The dispenser was loaded initially with about 100 grams of grease (10), with a density of about 900 kg/m³. Switch (24) was closed to turn the circuit on, and the unit operated at room temperature and zero kPa(gauge) grease outlet pressure. Over a period of 49 days, the current in the circuit ranged from an initial value of 0.49 mA to a final value of 0.28 mA. The graph of FIG. 6 shows a plot of grease volume dispensed as a function of time over the 49 day run. The approximate composition of total gas produced by the electrochemical cell over 49 days was as shown in Table 4.

TABLE 4

Gas Production

| Component | Volume % (dry basis) |
|---|---|
| hydrogen | 5.2 |
| oxygen | 0.3 |
| nitrogen | 66.4 |
| methane | 0.4 |
| carbon monoxide | 1.4 |
| carbon dioxide + nitrous oxide | balance |

EXAMPLE 10

The electrolytic cells of the invention may be housed as shown in FIG. 1A in a dispenser for a fluid 10. The dispenser has a body 12 and an outlet nozzle 14. There is a piston 16 and a bellows 18 to force the fluid 10 from the nozzle 14. The necessary force is generated by a electrolytic gas-generating cell 20 having an external circuit that includes a resistor 22 and a switch 24.

FIGS. 4A and 4B illustrate a housing for cells according to the present invention. The housing is of a sandwich construction optionally comprising an anode 36 in a conductive cup 38 (such as brass) having a contact 40 to enable wiring to an external circuit. There is an electrolyte 42 (which may be gelled) contained in a flexible, thin-walled tube 44 and a cathode 46 (which may be a screen) backed by a porous member such as graphite felt 48 to allow gas to escape, and a disk current collector 50 (which may be brass), with a contact 52 to enable wiring to the external circuit. The cell is contained in a an outer wall 54 (such as a polypropylene cylinder). There is a plastic spring washer 56 on cup 38 retained by a lip 60 on cylinder 54.

The combination of the spring loaded housing and the flexible, thin-walled electrolyte enclosure 44 allows the cells to contract over time as gas is evolved, which helps to ensure that the components of the cell remain in electrical contact. The use of the flexible, thin-walled enclosure 44 helps to prevent electrolyte from leaking from one cell to the next in multi-cell units, which could short-circuit the units. The electrolyte may also be gelled or absorbed in a solid to reduce its propensity to migrate, although the extent to which it is desirable to 'solidify' the electrolyte is limited by the need to permit species to migrate through the electrolyte during electrolysis.

FIG. 5 shows the configuration of a bi-cell. In multiple cell reactors, several of the cells shown in FIG. 4 are compressed in series with intimate electronic contact between adjacent anodes and cathodes. This contact is facilitated by the spring loading of the housing, such as with washer 56. A rigid wall, such as a polypropylene cylinder, may encompass the composite cell. Reference numerals are as in FIGS. 4A and 4B.

What is claimed is:

1. An electrolytic nitrogen gas generator comprising:
   a. a cathode and an anode connected as part of an electrical circuit that may be switched on or off;
   b. an electrolyte in contact with the anode comprising an active nitrogen compound selected from the group consisting of organic hydrazino carboxylates and amino guanidine salts;
   c. wherein nitrogen gas is generated at the anode from the active nitrogen compound when the electrical circuit is switched on.

2. The electrolytic nitrogen gas generator of claim 1, further comprising a cathode depolariser to suppress hydrogen generation.

3. The electrolytic nitrogen gas generator of claim 1, wherein the electrical circuit comprises a battery.

4. The electrolytic nitrogen gas generator of claim 1, wherein the electrical circuit comprises a resistor.

5. The electrolytic nitrogen gas generator of claim 4, wherein the resistor is a variable resistor.

6. The electrolytic nitrogen gas generator of claim 1, wherein the active nitrogen compound comprises methyl hydrazino-carboxylate.

7. The electrolytic nitrogen gas generator of claim 1, wherein the electrolyte comprises urea.

8. The electrolytic nitrogen gas generator of claim 1, wherein the electrolyte is an ionic compound selected from the group consisting of salts, acids and bases.

9. The electrolytic nitrogen gas generator of claim 8, wherein the ionic compound is selected from the group consisting of ammonium sulphate, sodium chloride, sulphuric acid.

10. The electrolytic nitrogen gas generator of claim 1, wherein the electrolyte is held in an absorbent material.

11. The electrolytic nitrogen gas generator of claim 10, wherein the absorbent material comprises an absorbent solid selected from the group consisting of sponges, felts and gels.

12. The electrolytic nitrogen gas generator of claim 10, wherein the absorbent material is selected from the group consisting of cellulose sponges and carbopol gels.

13. An electrolytic nitrogen gas generator comprising:
    a. a cathode and an anode connected as part of an electrical circuit that may be switched on or off;
    b. an electrolyte in contact with the anode comprising oxalic dihydrazide;
    c. wherein nitrogen gas is generated at the anode from oxalic dihydrazide when the electrical circuit is switched on.

14. The electrolytic nitrogen gas generator of claim 1, wherein the active nitrogen compound comprises aminoguanidine bicarbonate.

15. The electrolytic nitrogen gas generator of claim 1, wherein the electrolyte comprises aqueous sulphuric acid.

16. The electrolytic nitrogen gas generator of claim 1, wherein the electrolyte comprises an antifreeze.

17. The electrolytic nitrogen gas generator of claim 1, wherein the electrolyte comprises nitroethanol.

18. The electrolytic nitrogen gas generator of claim 1, wherein the electrolyte comprises nitromethane.

19. The electrolytic nitrogen gas generator of claim 1, wherein the electrolyte comprises nitroguanidine.

20. The electrolytic nitrogen gas generator of claim 1, wherein the electrolyte comprises a cupric salt.

21. The electrolytic nitrogen gas generator of claim 1, wherein the electrolyte comprises copper sulphate.

22. The electrolytic nitrogen gas generator of claim 1, wherein the anode comprises graphite.

23. The electrolytic nitrogen gas generator of claim 1, wherein the anode comprises graphite fibre impregnated with a polymer.

24. The electrolytic nitrogen gas generator of claim 1, further comprising an ion permeable membrane separating the cathode and a catholyte from the anode and the anolyte, wherein the ion permeable membrane electrically couples the catholyte to the anolyte.

25. The electrolytic nitrogen gas generator of claim 24 wherein the ion permeable membrane is selected from the group consisting of cation selective membranes and anion selective membranes.

26. The electrolytic nitrogen gas generator of claim 1, further comprising a bipolar electrode separating the cathode and a catholyte from the anode and the anolyte, wherein the catholyte electrically couples the cathode to the bipolar electrode and the anolyte electrically couples the bipolar electrode to the anode.

27. The electrolytic nitrogen gas generator of claim 26 further comprising an oxidant in contact with the cathode.

28. The electrolytic nitrogen gas generator of claim 27 wherein the oxidant is selected from the group consisting of manganese dioxide and a bromate salt.

29. The electrolytic nitrogen gas generator of claim 27 wherein the oxidant is sodium bromate.

30. The electrolytic nitrogen gas generator of claim 26 further comprising a reductant in contact with the bipolar electrode.

31. The electrolytic nitrogen gas generator of claim 30 wherein the reductant is selected from the group consisting of zinc powder and aluminium powder.

32. The electrolytic nitrogen gas generator of claim 26 wherein the electrolyte further comprises a depolariser for depolarising the cathode of the bipolar electrode.

33. The electrolytic nitrogen gas generator of claim 32 wherein the depolariser comprises a dissolved salt of a metal and the metal is deposited on the bipolar electrode to depolarise the bipolar electrode when the circuit is switched on.

34. The electrolytic nitrogen gas generator of claim 32 wherein the depolariser comprises a reducible organic compound selected from the group consisting of nitroethanol, nitromethane, and nitroguanidine.

35. The electrolytic nitrogen gas generator of claim 1 further comprising a transducer for capturing the nitrogen gas generated at the anode and producing mechanical energy therefrom.

36. The electrolytic nitrogen gas generator of claim 35, wherein the transducer is mechanically coupled to a fluid dispenser so that a fluid is dispensed from the fluid dispenser when nitrogen gas is generated at the anode.

37. An electrolytic nitrogen gas generator comprising:
    a. a cathode and an anode connected as part of an electrical circuit that may be switched on or off;
    b. an electrolyte in contact with the anode comprising an active nitrogen compound selected from the group consisting of organic hydrazides, organic hydrazino carboxylates and amino guanidine salts; the active nitrogen compound generating nitrogen gas at the anode when the electrical circuit is switched on; and c. a transducer for capturing the nitrogen gas generated at the anode and producing mechanical energy therefrom.

38. The electrolytic nitrogen generator of claim 37, wherein the transducer is mechanically coupled to a fluid dispenser so that a fluid is dispensed from the fluid dispenser when nitrogen gas is generated at the anode.

* * * * *